(12) United States Patent
Giordana et al.

(10) Patent No.: US 12,558,207 B2
(45) Date of Patent: Feb. 24, 2026

(54) SINGLE USE, ELONGATED TUBULAR SLEEVE FOR MEDICAL OR DENTAL INSTRUMENT

(71) Applicant: TIDI PRODUCTS, LLC, Neenah, WI (US)

(72) Inventors: Rebecca E. Giordana, Combined Locks, WI (US); John P. Wrass, Appleton, WI (US); Matthew J. Ondrus, Green Bay, WI (US); Chris W. Rahn, Appleton, WI (US); Amanda R. Altan, Neenah, WI (US); Anthony Steven Loftis Taylor, Oshkosh, WI (US)

(73) Assignee: TIDI Products, LLC, Neenah, WI (US)

( * ) Notice: Subject to any disclaimer, the term of this patent is extended or adjusted under 35 U.S.C. 154(b) by 238 days.

(21) Appl. No.: 18/292,146

(22) PCT Filed: Mar. 23, 2023

(86) PCT No.: PCT/US2023/016119
§ 371 (c)(1),
(2) Date: Jan. 25, 2024

(87) PCT Pub. No.: WO2023/183511
PCT Pub. Date: Sep. 28, 2023

(65) Prior Publication Data
US 2025/0000631 A1     Jan. 2, 2025

Related U.S. Application Data

(60) Provisional application No. 63/323,845, filed on Mar. 25, 2022.

(51) Int. Cl.
*A61C 13/15*        (2006.01)
*A61B 1/00*         (2006.01)
(Continued)

(52) U.S. Cl.
CPC ........ *A61C 19/004* (2013.01); *A61B 1/00142* (2013.01); *B32B 1/08* (2013.01);
(Continued)

(58) Field of Classification Search
CPC ..... A61C 19/004; A61C 1/16; A61B 1/00142; A61B 1/24; B32B 1/08; B32B 7/06;
(Continued)

(56) References Cited

U.S. PATENT DOCUMENTS 4,823,949 A     4/1989   Bala
4,846,344 A     7/1989   Bala
(Continued)

FOREIGN PATENT DOCUMENTS

WO     2014016221 A1     1/2014
WO     2015002552 A1     7/2015
WO     2015175928 A1     11/2015

OTHER PUBLICATIONS

PCT "Search Report and Written Opinion" for PCT/US23/16119 of Jul. 3, 2023, 8 pages filed herewith.
(Continued)

*Primary Examiner* — Amit Chatly
(74) *Attorney, Agent, or Firm* — Amundsen Davis, LLC

(57) ABSTRACT

A single use, elongated tubular sleeve for a medical or dental instrument. The sleeve includes first through fifth layers. The second layer has a distal end and being formed from about 70% to about 90% of a linear low-density polyethylene, from about 10% to about 20% of low-density polyethylene, from about 2% to about 3% of an anti-block agent, and about 2% of a slip additive. The third layer is formed identical in composition to that of the second layer. The fourth layer is formed from linear low-density polyethylene and exhibiting transparency and clarity with a haze less than 7.5%. The fifth layer is removably attached to both the first layer and to the
(Continued)

fourth layer, the first and fifth layers functioning as exterior protective layers for the second, third and fourth layers, and all adapted for placement over a medical or dental instrument to reduce the risk of contamination of the instrument.

20 Claims, 2 Drawing Sheets

(51) Int. Cl.

| | |
|---|---|
| *A61B 1/24* | (2006.01) |
| *B32B 1/08* | (2006.01) |
| *B32B 7/06* | (2019.01) |
| *B32B 27/08* | (2006.01) |
| *B32B 27/32* | (2006.01) |

(52) U.S. Cl.
CPC ................ *B32B 7/06* (2013.01); *B32B 27/08* (2013.01); *B32B 27/322* (2013.01); *A61B 1/24* (2013.01); *B32B 2250/05* (2013.01); *B32B 2250/242* (2013.01); *B32B 2250/40* (2013.01); *B32B 2323/046* (2013.01)

(58) Field of Classification Search
CPC ... B32B 27/08; B32B 27/322; B32B 2250/05; B32B 2250/242; B32B 2250/40; B32B 2323/046; B32B 7/02; B32B 2307/7376; B32B 2307/748; B32B 27/18; B32B 2270/00; B32B 2307/412; B32B 3/08; B32B 27/10; B32B 27/32; B32B 2307/746; B32B 2535/00; B32B 2597/00
See application file for complete search history.

(56) References Cited

U.S. PATENT DOCUMENTS

| | | | | |
|---|---|---|---|---|
| 5,069,337 | A | 12/1991 | Bala | |
| 5,107,988 | A | 4/1992 | Bala | |
| 5,406,939 | A | 4/1995 | Bala | |
| D731,652 | S | 6/2015 | Miller | |
| 9,433,468 | B2 | 9/2016 | Wilt et al. | |
| D827,137 | S | 8/2018 | Miller | |
| 2001/0008686 | A1 | 7/2001 | Inoue et al. | |
| 2005/0107870 | A1 | 5/2005 | Wang et al. | |
| 2006/0131190 | A1 | 6/2006 | Weaver et al. | |
| 2008/0154206 | A1 | 6/2008 | Guo et al. | |
| 2010/0063358 | A1* | 3/2010 | Kessler | A61B 1/00142 600/121 |
| 2012/0010468 | A1* | 1/2012 | Afridi | A61B 1/00142 600/121 |
| 2015/0202833 | A1 | 7/2015 | Miller et al. | |
| 2015/0230882 | A1* | 8/2015 | Miller | A61B 46/10 433/29 |
| 2021/0324185 | A1 | 10/2021 | Li et al. | |
| 2024/0197153 | A1* | 6/2024 | Salman | A61B 1/00142 |

OTHER PUBLICATIONS

Supplementary European Search Report for Application No. 23775679.6 and issued on Jun. 5, 2025, 30 pages filed herewith.
English Translation of WO2014016221A1, received Jun. 5, 2025, 25 pages filed herewith.

\* cited by examiner

SINGLE USE, ELONGATED TUBULAR SLEEVE FOR MEDICAL OR DENTAL INSTRUMENT

CROSS-REFERENCE TO RELATED APPLICATION

This application claims the benefit of U.S. Provisional Application No. 63/323,845, filed Mar. 25, 2022, and titled: SINGLE USE, ELONGATED TUBULAR SLEEVE FOR A MEDICAL OR DENTAL INSTRUMENT.

FIELD OF THE INVENTION

This invention relates to a, preferably, single use elongated tubular sleeve for a medical or dental instrument. The elongated tubular sleeve can cover and form a barrier for instruments such as probes, cameras and curing devices used in medical and dental procedures in an animal like a human.

BACKGROUND OF THE INVENTION

Various types of sleeves, barriers, sheaths or other covers are frequently used with a variety of medical and dental instruments that come in close contact with a patient's body, for example, dental curing lights and cameras. Especially in instances where the medical or dental instrument enters the patient's body or body cavity, the instrument must be disinfected before it can be reused to avoid the spread of germs and disease. Disinfection can be expensive and time consuming, and thus use of a sleeve that can be easily thrown away after use is appealing. As these sleeves are disposable, they must be affordably manufactured. However, while the sleeve must be affordable, it must be durable so that it does not rip or tear when applied to the medical or dental equipment or during use thereof. Obviously, a fitted sleeve is preferred as this will minimize the impact of the sleeve on the doctor or dentist's ability to efficiently perform the procedure. This is especially true where the sleeve is used with a dental curing light or camera because a tight-fitting sleeve will reduce the risk of obstruction of transmitted light through the sleeve or viewing image such as with a camera.

Now a new form of, preferably, single use elongated tubular sleeve has been invented that is made from inexpensive material and which forms a fitted relationship with the medical or dental instrument to which it is affixed to help reduce the spread of infectious diseases from multiple use of the same instrument.

SUMMARY OF THE INVENTION

This invention aids to provide an elongated tubular sleeve which can cover a variety of medical and dental instruments, especially hand-held instruments. More specifically, this invention can aid to provide an elongated tubular sleeve which forms a fitted relationship with medical or dental instrument to help prevent the spread of germs and diseases.

This invention can aid to provide a single use, elongated tubular disposable sleeve which can be discarded after a single use.

This invention further can aid to provide a single use, elongated tubular sleeve which is easy to manufacture.

This invention can also aid to provide a single use, elongated tubular sleeve which forms a highly effective viral protection for an instrument that enters a patient's body or body cavity, like the mouth.

In one aspect, there is provided a single use, elongated tubular sleeve for a medical or dental instrument. The sleeve includes a first through a fifth layer. The second layer has a distal end and is formed from about 70% to about 90% of a linear low-density polyethylene, from about 10% to about 20% of low-density polyethylene, from about 2% to about 3% of an anti-block agent, and about 2% of a slip additive, the second layer having a thickness ranging from between about 1.36 mils to 1.64 mils, and having a coefficient of friction equal to or less than about 0.35. The third layer is formed identical in composition to that of the second layer, the third layer having a thickness of about 0.86 mils to about 1.14 mils and having a distal end spaced inward from the distal end of the second layer. The fourth layer is formed from linear low-density polyethylene and exhibiting transparency and clarity with a haze less than 7.5%, the fourth layer being secured to the second and third layers, the fourth layer having a thickness of about 1.24 mils to about 1.5 mils, the fourth layer having a distal end coterminous with the distal end of the second layer. The fifth layer is removably attached to both the first layer and to the fourth layer, the first and fifth layers functioning as exterior protective layers for the second, third and fourth layers, the second, third and fourth layers forming an elongated structure with a closed distal end, an open proximal end, closed lateral seals, and an inner surface surrounding a volume adapted for placement over a medical or dental instrument to reduce the risk of contamination of the instrument.

In another aspect, there is provided a single use, elongated tubular sleeve for a medical or dental instrument. The sleeve includes a first through a fifth layer. The first layer is formed from a polymeric material. The second layer is formed from about 75% to about 85% of a linear low-density polyethylene, from about 13% to about 17% of low-density polyethylene, about 2% of an anti-block agent, and about 2% of a slip additive, the second layer having a thickness ranging from between about 1.36 mil to 1.64 mils, and having a coefficient of friction equal to or less than about 0.35. The third layer is formed identical in material composition to that of the second layer, the third layer having a thickness of about 0.95 mils to about 1.05 mils and having a distal end spaced inward from the distal end of the second layer. The fourth layer formed from linear low-density polyethylene and exhibiting transparency and clarity with a haze less than about 7.5%, the fourth layer being secured to the second and third layers, the fourth layer having a distal end coterminous with the distal end of the second layer, and the fourth layer having a thickness of about 1.3 mils to about 1.45 mils. The fifth layer removably attached to both the first layer and to the fourth layer, the first and fifth layers functioning as exterior protective layers for the second, third and fourth layers, the second, third and fourth layers forming an elongated structure with a closed distal end, an open proximal end, closed lateral seals, and an inner surface surrounding a volume adapted for placement over a medical or dental instrument to reduce the risk of contamination of the instrument. Other features and advantages of the present invention will become more apparent to those skilled in the art in view of the following description and the accompanying drawings.

3

Figures 1, 2, 3, 4:
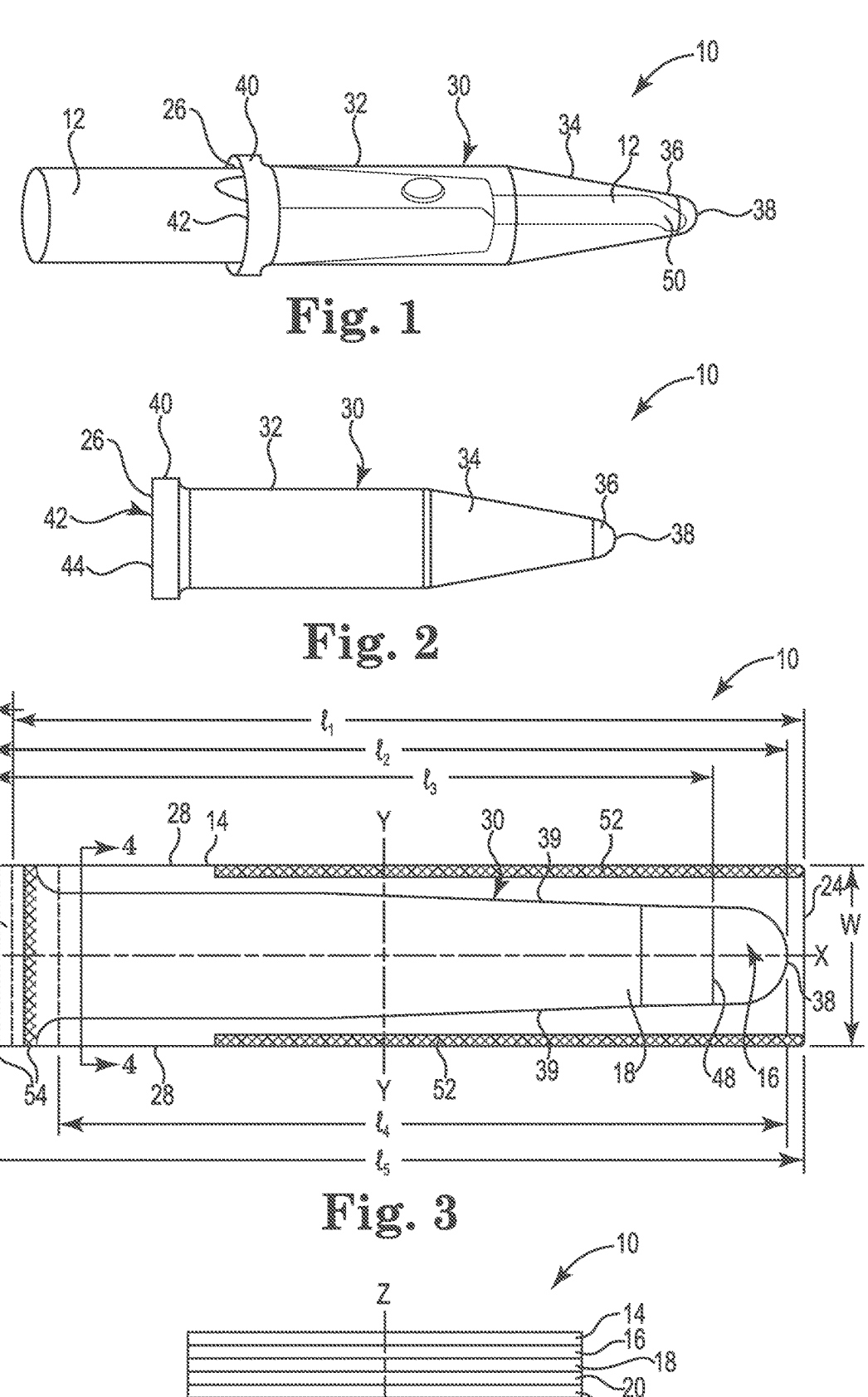
FIG. 1 is an isometric view of an elongated tubular sleeve for medical or dental instruments enclosing a major portion of a dental curing light.

FIG. 2 is a side view of the tubular sleeve shown in FIG. 1.

FIG. 3 is a top view of the tubular sleeve showing various seals.

FIG. 4 is an end view of FIG. 3 taken along line 4-4.

Figure 5:
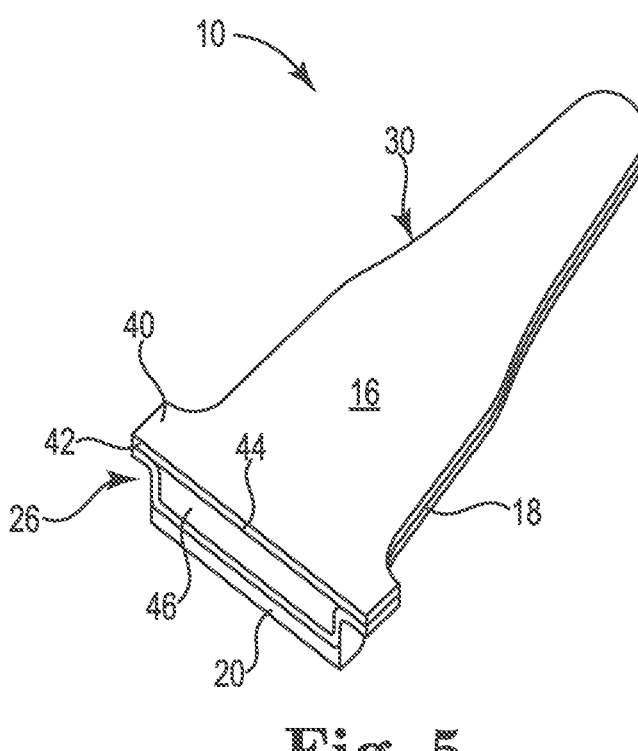

FIG. 5 is a perspective view of the middle three layers of the tubular sleeve of FIG. 1 without the dental curing light inserted therein.

DETAILED DESCRIPTION OF THE INVENTION

Referring to FIGS. 1-5, an elongated flexible tubular sleeve 10 is shown which can be form fitted with a variety of different medical or dental instruments 12. Preferably, sleeve 10 is a single use, to aid in sanitation and use as intend in a medical or dental practice. In FIG. 1 the instrument 12 is depicted, for example, as a dental curing light which is used to cure resin used to fill a tooth cavity. It should be understood that many different kinds of hand-held medical or dental instruments could be protected by a single use, elongated tubular sleeve 10. The size, shape and configuration of the single use, elongated, flexible tubular sleeve 10 can be varied to fit a particular instrument. The elongated tubular sleeve 10 has an inner surface 46, see FIG. 5, surrounding a volume adapted for placement over a medical or dental instrument 12 to reduce the risk of contamination of the instrument.

Referring to FIGS. 3 and 4, the single use, elongated tubular sleeve 10 is shown having an initial flat, rectangular configuration. The sleeve 10 has a longitudinal central axis X-X, a vertical central axis Y-Y, and a transverse central axis Z-Z. The sleeve 10 can contain five layers, for example, denoted as a first layer 14, a second layer 16, a third layer 18, a fourth layer 20 and a fifth layer 22. The first layer 14 is the upper most layer and the fifth layer 22 is the lower most layer. The single use, elongated tubular sleeve 10 has a distal end 24, an open proximal end 26, and a pair of lateral sides 28, 28. The first and fifth layers, 14 and 22 respectively, are exterior layers which are designed to reduce potential contamination to the inner three layers 16, 18 and 20 f prior to using the sleeve 10 to protect an instrument 12. The first and fifth layers, 14 and 22 respectively, are designed to be removed from the inner three layers 16, 18 and 20 once the instrument 12 is inserted between the second and third layers, 16 and 18 respectively.

Referring now to FIGS. 1-5, the second, third and fourth layers 16, 18 and 20 respectively, have a tubular structure 30. The tubular structure is best depicted in FIG. 5 after the first and fifth layers, 14 and 22 respectively, are removed. The tubular structure 30 has a number of sections. As best seen in FIG. 2, four sections 32, 34, 36 and 38 are depicted and are arranged from left to right. Other embodiments of the sleeve 10 may have fewer or greater number of sections, if desired. The sections 32, 34, 36 and 38 of the tubular structure 30 will have varying circumferences that are selected to fittingly accommodate varying sizes of medical or dental instruments 12. Depending on the design of the medical or dental instrument 12, each of the sections 32, 34, 36 and 38 can vary in shape and can have a tapered or a constant circumference. The tubular structure 30 may have numerous configurations such that it will be shaped to accept medical and dental instruments 12 of varying sizes and shapes. The last section 38 has a rounded shape and is spaced inward from the distal end 24 of the sleeve 10, see FIG. 3. The rounded section 38 can be spaced about 0.1 inches or more inward from the distal end 24. The tubular structure 30 also has a pair of closed lateral sides 39, 39. The lateral sides 39, 39 of the second, third and fourth layers, 16, 18 and 20 respectively, can be secured together using heat, heat and pressure, an adhesive, or by any other means known to those skilled in the art in combination with the teaching herein. The pair of lateral sides 39, 39 join together flexible plastic film layers, e.g., made of polyethylene or the like as described further herein. Desirably, the second, third and fourth layers, 16, 18 and 20 respectively, are secured together by a heat seal. The lateral sides 39, 39 are permanently sealed or bonded together and cannot be easily broken except by destructively tearing the material from which each layer is formed.

Referring now to the left portion of FIGS. 1 and 2, a ring section 40 may be positioned at the open proximal end 26 of the second layer 16. The ring section 40 extends away from the closed distal end 24. The ring section 40 begins with a circumference equal to the circumference at the end of the tubular structure 30 and extends to a greater circumference that will better facilitate insertion of the medical or dental instrument 12 into sleeve 10. Desirably, the ring section 40 will have a grip 42 that is made of a heavier plastic material than the remaining portions of sleeve 10. This heavier plastic material can still stretch but provides more rigidity than the remaining portions of the sleeve 10. Unlike the other parts of the sleeve 10, the material of the grip 42 of the ring section 40 is not transparent, and is desirably opaque. This makes it easier for a user to visually identify when trying to open the sleeve 10 for insertion of the medical or dental instrument 12 between the second and third layers, 16 and 18 respectively. This also allows the user to easily grip the ring section 40 and open the proximal end 26 of the sleeve 10. Additionally, the ring section 40 has a portion 44, spaced apart from the grip 42, that extends beyond the length of the grip 42. The portion 44 can also be gripped. This allows a user to insert the medical or dental instrument 12 into the tubular structure 30, between the grip 42 and the portion 44. Referring to FIG. 3, one will notice two bar seals 54, 54 formed across the width of the sleeve 10 and adjacent to the proximal open end 26. The bar seals 54, 54 function to secure the ring section 40 to the second layer 16 and to secure the fourth layer 20 to the fifth layer 22.

Referring to FIG. 5, in practice, the medical or dental instrument 12 will first be positioned into the ring section 40, between the second and third layers, 16 and 18 respectively, and then be further inserted into the tubular structure 30. Each sleeve 10 has an inner surface 46 configured to surround a volume and accept the medical or dental instrument 12. By so inserting the medical or dental instrument 12, one can to reduce the risk of contamination of the instrument, which may This will be especially useful when the medical or dental instrument 12 is used on multiple patients in a short period of time.

Referring again to FIGS. 3 and 4, the first layer 14 of the single use, elongated tubular sleeve 10 has a rectangular configuration with a length $l_1$ and a width w. The length $l_1$ can vary. A length $l_1$ of about 9.5 to 10.75 inches, for example 10.25 inches, is adequate to accommodate a standard size dental curing light instrument 12. The width w can also vary. A width w of about 2.25 to about 3.5 inches, for example 2.75 inches, is adequate to accommodate a standard size dental curing light instrument 12.

The first layer 14 can be made from a variety of different materials. A polymeric material, such as polyethylene provides several advantages for this particular layer. First, polyethylene is relatively inexpensive, which is important as the sleeves 10 are only used once before disposal. Second, polyethylene has sufficient elastic material memory to maintain itself. Third, polyethylene has enough elasticity to allow the sleeve to stretch without breaking. Fourth, polyethylene can be heat sealed relatively easily. Fifth, polyethylene can exhibit a degree of clarity and is relatively transparent. Lastly, polyethylene can be printed, if desired.

Referring now to FIGS. 1-5, one will notice that the shape and configuration of the second, third and fourth layers, 16, 18 and 20 respectively, are not rectangular. Instead, they form the tubular structure 30, as mentioned above. In addition, the second layer 16 has a length $l_2$ which is different from the length $l_1$ of the first layer 14. This length $l_2$ is spaced inward from the distal end 24 of the sleeve 10 by about 0.1 inches or more. The length $l_2$ is also spaced inward from the proximal open end of the sleeve 10. The second layer 16 has a width which varies along its length $l_2$. However, at the proximal open end 26, the width of the second layer 16 is equal to the width w of the first layer 14.

The composition of the second layer 16 is believed to be completely different from any currently available medical or dental instrument sleeve. After extensive experimentation, a composition for the second layer 16 has been surprisingly found to provide exceptional performance characteristics. The composition of the second layer 16 contains from between about 70% to about 90% of a linear low-density polyethylene (LLDPE). Desirably, the second layer 16 is formed from between about 75% to about 85% of LLDPE. More desirably, the second layer 16 is formed from between about 77% to about 83% of a LLDPE. Even more desirably, the second layer 16 is formed from between about 79% to about 82% of a LLDPE. Still more desirably, the second layer 16 is formed from about 81% of a LLDPE.

LLDPE is a substantially linear polymer, with significant numbers of short branches, commonly made by copolymerization of ethylene with longer-chain olefins. LLDPE differs from low-density polyethylene (LDPE) in that LLDPE is a copolymer of ethylene and another longer olefin, which is incorporated to improve properties such as tensile strength, tear strength, puncture resistance or resistance to harsh environments. American Society for Testing and Materials (ASTM) test D882 can be used to measure tensile strength. Likewise, ASTM test D1004 can be used to measure tear strength and ASTM test F1342 can be used to measure puncture resistance.

LLDPE further provides excellent viral protection. By "viral protection" it is meant preventing contamination of the instrument by blood or other body fluids through the sleeve 10 and onto the instrument 12. American Society for Testing and Materials (ASTM) test F1671 can be used to measure viral penetration values of a plastic film or layers of film forming a composite material. ASTM test F1670 can be used to measure blood penetration values of a film.

Additionally, a slip agent can be added to the LLDPE. The slip agent will allow a user to more easily and smoothly insert a medical or dental instrument 12 into the tubular structure 30 of the sleeve 10. Furthermore, an anti-block agent can be added to the LLDPE. The anti-block agent will increase the processability of the tubular structure 30 during manufacture. Another feature of LLDPE is that it is a non-hazardous material and it's over exposure by short term or long term inhalation does not cause any harmful health effects. LLDPE can provide better penetration protection than a copolymer. LLDPE is commercially available from a variety of suppliers. Westlake, having a mailing address of 2801 Post Oak Blvd., Suite 600 Houston, Texas 77056 USA is one such supplier that sells a LLDPE under the product code: "LF1050AA". This particular product, for example, is useful in constructing the single use, elongated tubular sleeve 10.

The composition of the second layer 16 also, preferably, contains from about 10% to about 20% of LDPE. LDPE, on the other hand, is a homopolymer constituted by ethylene monomers. The use of about 13% to about 17% of a LDPE in the second layer is more preferred. And, the use of about 15% of a LDPE in the second layer is even more preferred. For example, LDPE is added to the second layer 16 to improve its ability to be processed and manufactured. LDPE is commercially available from a variety of suppliers. ExxonMobil Chemical Company, having a mailing address of 22777 Springwoods Village Parkway Spring, Texas 77389-1425, USA is one such supplier that sells low-density polyethylene under the product code: "LD4001". This particular product, for example, is useful in constructing the single use, elongated tubular sleeve 10. Further, preferable and advantageously, the LDPE assists in the formation of a stable bubble, which is desired in order to extrude the resin into a film. The stable bubble is also beneficial in providing a more consistent film throughout the manufacturing process.

The composition of the second layer 16 further contains an anti-block agent. Anti-block agents assist in minimizing surfaces from interacting with one another either through adhesion or other adhesion-like forces. These materials form barriers between surface layers and modify the frictional properties of the surface. The presence of an anti-block agent helps create slight imperfections in the film which can affect its overall smoothness. While a smooth film is desirable, the inventors have found that reducing the amount of the anti-block agent too much negatively impacts the handleability of adjacent film layers. Conversely, having too much anti-block can then lead to permeability and/or transmissibility of pathogens (e.g., bacteria, viruses, etc.) more easily through the film layer. Thus, the inventors have surprisingly found a particular range for the amount of anti-block that should be used in the second layer 16 of the sleeve 10, a range that properly balances the potentially negative impacts of too much and too little anti-block agent in the second layer. The percentage of the anti-block agent present in the second layer 16 is preferably between about 2% and about 3%. Desirably, the percentage of the anti-block agent present in the second layer 16 is more than about 2% and less than about 2.75%. More desirably, the percentage of the anti-block agent present in the second layer 16 is more than about 2% and less than about 2.5%. Even more desirably, the percentage of the anti-block agent present in the second layer 16 is more than about 2% and less than about 2.25%. Most desirably, the percentage of the anti-block agent present in the second layer 16 is about 2.1%. Anti-block agents are commercially available from a variety of suppliers. Ampacet, having a mailing address of Global Headquarters, 660 White Plains Road, Tarrytown, New York 10591, United States is one such supplier that sells an anti-block agent under the product code: "AD4210". This particular product is useful in constructing the single use, elongated tubular structure 30.

The composition of the second layer 16 further contains a slip additive. Slip additives are products which can be added to polymers to control friction, i.e., decrease the frictional impact at the outer surface of a film layer. They are added directly into the polymer during the extrusion process and migrate to the surface as the polymer cools, allowing a solid lubricating layer to form. Like with the anti-block agent, the inventors have surprisingly found a particular range for the amount of slip additive that should be used in the second layer 16 of the sleeve 10, a range that properly balances the potentially negative impacts of too much and too little slip additive in the second layer. For example, second layer 16 preferably has about 2% of slip additive. Slip additives are commercially available from a variety of suppliers. Ampacet, having a mailing address of Global Headquarters, 660 White Plains Road, Tarrytown, New York 10591, United States is one such supplier that sells a slip agent under the product code: "AD4200". This particular product is useful in constructing the single use, elongated tubular sleeve 10.

Besides the material composition of the second layer 16, the thickness of the second layer 16 is important. The thickness of the second layer 16 should range from between about 1.36 mils to about 1.64 mils. A mil is defined as a unit of length equal to one thousandth of an inch (i.e., and equivalently 0.0254 millimeters). The unit "mils" is commonly used to specify the thickness of very thin films. Desirably, the thickness of the second layer 16 should range from between about 1.4 mils to about 1.6 mils. More desirably, the thickness of the second layer 16 should range from between about 1.45 mils to about 1.55 mils. Even more desirably, the thickness of the second layer 16 should range from between about 1.47 mils to about 1.53 mils.

A third important characteristic of the second layer 16 is its coefficient of friction (COF). Coefficient of friction (fr) is a number that is the ratio of the resistive force of friction (Fr) divided by the normal or perpendicular force (N) pushing the objects together. For example, this can be better obtained and/or controlled by the amount of slip additive used. Mathematically, $fr=Fr/N$. Generally, the lower the COF value would be the most preferable. So, 0.15 would be more ideal than a 0.30 value and so on. However, as with the anti-block agent and the slip additive, the inventors have surprisingly found a particular range for the desired COF that should be used in the second layer 16 of the sleeve 10, a range that properly balances the potentially negative impacts of too much and too little COF in the second layer. The COF of the second layer 16 is equal to or less than about 0.35. The COF of the second layer 16 preferably ranges from between about 0.1 to about 0.35. More preferably, the COF of the second layer 16 ranges from between about 0.15 to about 0.3. Even more preferably, the COF of the second layer 16 ranges from between about 0.2 to about 0.3. Still more preferably, the COF of the second layer 16 ranges from between about 0.25 to about 0.3. American Society for Testing and Materials (ASTM) test D1894 can be used to measure COF values of the film layers of this invention.

Still referring to FIG. 3, the third layer 18 will now be described. The third layer 18 has a length $l_3$. The length $l_3$ extends beyond the second layer 16 very slightly adjacent to the proximal end 26 and terminates at a distal end 48. Stated another way, the third layer 18 is spaced inward from the distal end 38 of the second layer 16. The medical or dental instrument 12 is designed to be inserted in between the second and third layers 16 and 18 respectively.

The material composition of the third layer 18 is the same as that of the second layer 16. In addition, the COF of the third layer 18 is identical to that of the second layer 16. It should be understood that the second and third layers, 16 and 18 respectively, have the same COF so as to allow a user to more easily slide a medical or dental instrument 12 between these two layers, and making manufacturing easier with identical material composition.

The thickness of the third layer 18 is, preferably, less than the thickness of the second layer 16. The third layer 18 preferably has a thickness ranging from between about 0.86 mils to about 1.14 mils. Desirably, the thickness of the third layer 18 ranges from between about 0.9 mils to about 1.1 mils. More desirably, the thickness of the third layer 18 ranges from between about 0.95 mils to about 1.05 mils. Even more desirably, the thickness of the third layer 18 ranges from between about 0.97 mils to about 1.03 mils. Most desirably, the thickness of the third layer 18 is about 1 mil. The thickness of the third layer 18 can be less than that of the second layer 16, preferably, because of the presence of the fourth layer 20.

Referring again to FIG. 3, the fourth layer 20 will now be described. The fourth layer 20 has a length $l_4$. The length $l_4$ extends from a location slightly inward of the proximal end of the second layer 16 and terminates at the distal end 38. The distal end 38 is spaced inward from the distal end 24 of the sleeve 10. The fourth layer 20 has a shape and configuration that is similar to the second layer 16 and third layer 18. The fourth layer 20 is spaced inward from the proximal open end 26. This difference in length at the proximal open end 26 facilitates a user inserting a medical or dental instrument 12 between the second and third layers, 16 and 18 respectively. One cannot insert the medical or dental instrument between the third and fourth layers, 18 and 20 respectively, because the fourth layer 20 is spaced inward at the proximal end 26 and is temporarily bonded or sealed to the fifth layer 22.

It should be understood that the third layer 18 is shorter at the distal section 38 than the second and fourth layers, 16 and 20 respectively. This means that whatever emanates from the tip of the medical or dental instrument 12, whether it be a curing light or a lens for a camera, does not pass through this distal end of the third layer 18. For example, an instrument 12 having a camera mounted at one end thereof will benefit by not having the image pass through two layers. By passing the image through only the fourth layer 20, one may be able to obtain sharper images.

In addition, the composition of the fourth layer 20 is different from that of the second and third layers, 16 and 18 respectively. The fourth layer 20 is constructed of a LLDPE but it does not include an anti-block agent or a slip agent. In other words, the fourth layer 20 is free from these two agents. Desirably, the fourth layer 20 is 100% LLDPE. LLDPE is commercially available from a variety of suppliers. Westlake, having a mailing address of 2801 Post Oak Blvd., Suite 600 Houston, Texas 77056 USA, as one such supplier that sells a LLDPE under the product code: "LF74580". This particular product is useful in constructing the single use, elongated tubular sleeve 10.

The fourth layer 20 preferably exhibits good clarity and transparency. Clarity is measured by an inverse property, namely, haze. For haze testing (using ASTM test D1003, procedure A), preferably the fourth layer has a haze of less than or equal to 7.5%. More preferably, the haze is no greater than 7.3%. Even more preferably, the haze is no more than 7% and most preferably the haze value is no more than about 6.8%. While zero haze is theoretically the best, the inventors have surprisingly found a particular range for the desired haze that should be used in the fourth layer 20 of the sleeve 10, a range that properly balances the potentially negative impacts of too much and too little haze in the fourth layer. The fourth layer 20 has a haze that is better than the second and third layers 16 and 18 respectively. By "haze" it is meant the quality of transparency. By "transparent" it is meant that the material allows more light to readily pass through so that an object behind can be seen more clearly by one of ordinary skill in the art having 20/20 vision.

Lastly, the thickness of the fourth layer 20 is also important. The thickness of the fourth layer 20 should range from between about 1.24 mils to about 1.5 mils. Desirably, the thickness of the fourth layer 20 should range from between about 1.3 mils to about 1.45 mils. More desirably, the thickness of the fourth layer 20 should range from between about 1.32 mils to about 1.4 mils. Even more desirably, the thickness of the fourth layer 20 should range from between about 1.34 mil to about 1.38 mils. In another aspect, additionally or alternatively, the thickness of the fourth layer 20 is less than the thickness of the second layer 16 but is greater than the thickness of the third layer 18. For example, the thickness of the third layer 18 can be less than that of the second layer 16 because it is sealed, such as by a heat seal, to the fourth layer 20 and will gain rigidity therefrom.

Referring again to FIG. 3, the fifth layer 22 of the single use, elongated tubular sleeve 10 has a rectangular configuration. The fifth layer 22 has a length $l_5$ and a width w. The fifth layer 22 is coterminous with the first layer 14 at the distal end 14 and at the proximal end 26, the fifth layer 22 extends beyond the length d of the first layer 14. The length $l_5$ of the fifth layer 22 is also longer than the length $l_2$ of the second layer 16 or the length $l_4$ fourth layer 20. In addition, the length $l_5$ of the fifth layer 22 is also longer than the length $l_3$ of the third layer 18. The length $l_5$ of the fifth layer 22 can be about 8 to 10 inches, for example about 8.75 inches, when the sleeve 10 is designed to receive a standard size dental curing light instrument 12. The width w of the fifth layer 22 is equal to the width w of the first layer 14. The fifth layer 22 can be formed from various materials. Paper, a polymeric material, or a composite material could be used to construct the fifth layer 22. Desirably, the fifth layer 22 is formed from paper. Paper is relatively inexpensive and can be easily cut to a desired size. It is also relatively easy to recycle paper.

Still referring to FIG. 3, the fifth layer 22 can be removably attached to both the first layer 14 and to the fourth layer 20 by a seal, a thermal bond, a heat seal, a heat and pressure seal, by an adhesive or by some other means known to those skilled in the art. Desirably, the fifth layer 22 is heat sealed to the first layer 14 and to the fourth layer 20. In FIG. 3, a pair of pouch seals 52, 52 temporarily seal or bond the first layer 14 to the fifth layer 22. The pouch seals 52, 52 are aligned along the pair of lateral sides 28, 28 of the sleeve 10. The first and fifth layers, 14 and 22 respectively, function as temporary exterior protective layers for the tubular structure 30 until after the medical or dental instrument 12 is inserted between the second and third layers, 16 and 18 respectively. The first layer 14 can then be removed followed by the removal of the fifth layer 22. The first and fifth layers, 14 and 22 respectively, can be properly discarded.

After Use of the Sleeve

After the elongated tubular sleeve 10 has performed its function of protecting the medical or dental instrument 12 from blood, saliva or other bodily fluids, it can be removed from the instrument 12. The elongated tubular sleeve 10 is then be properly disposed of in a waste container. Since the tubular sleeve 10 may be contaminated with a patient's blood, saliva or other bodily fluids, it should be properly disposed in a waste container designed to receive medical waste products.

Each and every document cited in this present application, including any cross referenced or related patent or application, is incorporated in this present application in its entirety by this reference, unless expressly excluded or otherwise limited. The citation of any document is not an admission that it is prior art with respect to any embodiment disclosed in this present application or that it alone, or in any combination with any other reference or references, teaches, suggests, or discloses any such embodiment. Further, to the extent that any meaning or definition of a term in this present application conflicts with any meaning or definition of the same term in a document incorporated by reference, the meaning or definition assigned to that term in this present application governs.

The present invention includes the description, examples, embodiments, and drawings disclosed; but it is not limited to such description, examples, embodiments, or drawings. As briefly described above, the reader should assume that features of one disclosed embodiment can also be applied to all other disclosed embodiments, unless expressly indicated to the contrary. Unless expressly indicated to the contrary, the numerical parameters set forth in the present application are approximations that can vary depending on the desired properties sought to be obtained by a person of ordinary skill in the art without undue experimentation using the teachings disclosed in the present application. Modifications and other embodiments will be apparent to a person of ordinary skill in the art here, and all such modifications and other embodiments are intended and deemed to be within the scope of the present invention.

What is claimed is:

1. A single use, elongated tubular sleeve for a medical or dental instrument comprising:
   a) a first layer;
   b) a second layer having a distal end and being formed from about 70% to about 90% of a linear low-density polyethylene, from about 10% to about 20% of low-density polyethylene, from about 2% to about 3% of an anti-block agent, and about 2% of a slip additive, the second layer having a thickness ranging from between about 1.36 mils to 1.64 mils, and having a coefficient of friction equal to or less than about 0.35;
   c) a third layer formed identical in composition to that of the second layer, the third layer having a thickness of about 0.86 mils to about 1.14 mils and having a distal end spaced inward from the distal end of the second layer;
   d) a fourth layer formed from linear low-density polyethylene and exhibiting transparency and clarity with a haze less than 7.5%, the fourth layer being secured to the second and third layers, the fourth layer having a thickness of about 1.24 mils to about 1.5 mils, the fourth layer having a distal end coterminous with the distal end of the second layer; and
   e) a fifth layer removably attached to both the first layer and to the fourth layer, the first and fifth layers functioning as exterior protective layers for the second, third and fourth layers, the second, third and fourth layers forming an elongated structure with a closed distal end, an open proximal end, closed lateral seals, and an inner surface surrounding a volume adapted for placement over a medical or dental instrument to reduce the risk of contamination of the instrument.

2. The single use, elongated tubular sleeve of claim 1 wherein the fourth layer is free of any additive.

3. The single use, elongated tubular sleeve of claim 1 wherein the second layer has a thickness ranging from between about 1.4 mils to about 1.6 mils.

4. The single use, elongated tubular sleeve of claim 1 wherein the second layer has a thickness of about 1.5 mils.

5. The single use, elongated tubular sleeve of claim 1 wherein the second layer has a distal end, and the third layer has a distal end which is spaced inward from the distal end of the second layer by at least about 0.3 inches.

6. The single use, elongated tubular sleeve of claim 5 wherein the second layer has a distal end, and the fourth layer has a distal end which is coterminous with the distal end of the second layer.

7. The single use, elongated tubular sleeve of claim 6 wherein the second layer has a length which is longer than the length of the third layer.

8. The single use, elongated tubular sleeve of claim 1 wherein the thickness of the second layer is greater than the thickness of the third layer.

9. The single use, elongated tubular sleeve of claim 1 wherein the thickness of the fourth layer is greater than the thickness of the third layer.

10. A single use, elongated tubular sleeve for a medical or dental instrument comprising:

a) a first layer formed from a polymeric material;

b) a second layer formed from about 75% to about 85% of a linear low-density polyethylene, from about 13% to about 17% of low-density polyethylene, about 2% of an anti-block agent, and about 2% of a slip additive, the second layer having a thickness ranging from between about 1.36 mil to 1.64 mils, and having a coefficient of friction equal to or less than about 0.35;

c) a third layer formed identical in material composition to that of the second layer, the third layer having a thickness of about 0.95 mils to about 1.05 mils and having a distal end spaced inward from the distal end of the second layer;

d) a fourth layer formed from linear low-density polyethylene and exhibiting transparency and clarity with a haze less than about 7.5%, the fourth layer being secured to the second and third layers, the fourth layer having a distal end coterminous with the distal end of the second layer, and the fourth layer having a thickness of about 1.3 mils to about 1.45 mils; and e) a fifth layer removably attached to both the first layer and to the fourth layer, the first and fifth layers functioning as exterior protective layers for the second, third and fourth layers, the second, third and fourth layers forming an elongated structure with a closed distal end, an open proximal end, closed lateral seals, and an inner surface surrounding a volume adapted for placement over a medical or dental instrument to reduce the risk of contamination of the instrument.

11. The single use, elongated tubular sleeve of claim 10 wherein the fourth layer is free of any additive.

12. The single use, elongated tubular sleeve of claim 10 wherein the second layer has a thickness ranging from between about 1.4 mils to about 1.6 mils.

13. The single use, elongated tubular sleeve of claim 10 wherein the second layer has a thickness of about 1.5 mils.

14. The single use, elongated tubular sleeve of claim 10 wherein the second layer has a distal end, and the third layer has a distal end which is spaced inward from the distal end of the second layer by at least about 0.3 inches.

15. The single use, elongated tubular sleeve of claim 14 wherein the second layer has a distal end, and the fourth layer has a distal end which is coterminous with the distal end of the second layer.

16. The single use, elongated tubular sleeve of claim 15 wherein the second layer has a length which is longer than the length of the third layer.

17. The single use, elongated tubular sleeve of claim 10 wherein the thickness of the second layer is greater than the thickness of the third layer.

18. The single use, elongated tubular sleeve of claim 10 wherein the thickness of the fourth layer is greater than the thickness of the third layer.

19. The single use, elongated tubular sleeve of claim 10 wherein the third layer has a thickness of about 1 mil.

20. The single use, elongated tubular sleeve of claim 10 wherein the fourth layer has a thickness of about 1.34 mils to about 1.38 mils.

* * * * *